(12) United States Patent
Anderson

(10) Patent No.: US 7,573,258 B2
(45) Date of Patent: Aug. 11, 2009

(54) COIL ARRANGEMENT FOR ELECTROMAGNETIC TRACKER METHOD AND SYSTEM

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 9 days.

(21) Appl. No.: 11/654,880

(22) Filed: Jan. 18, 2007

(65) Prior Publication Data

US 2008/0174304 A1 Jul. 24, 2008

(51) Int. Cl.
*H01F 5/00* (2006.01)
*A61B 5/06* (2006.01)

(52) U.S. Cl. .............. 324/207.17; 324/207.16; 600/424

(58) Field of Classification Search ............ 324/207.12, 324/207.13, 207.15, 207.16, 207.17, 207.23, 324/207.26; 600/424; 128/899
See application file for complete search history.

(56) References Cited

U.S. PATENT DOCUMENTS

| | | | |
|---|---|---|---|
| 1,450,080 A | 3/1923 | Hazeltine | |
| 4,710,708 A | 12/1987 | Rorden | |
| 4,849,692 A | 7/1989 | Blood | |
| 4,945,305 A | 7/1990 | Blood | |
| 5,425,382 A | 6/1995 | Golden | |
| 5,558,091 A | 9/1996 | Acker | |
| 5,592,939 A | 1/1997 | Martinelli | |
| 5,640,170 A | 6/1997 | Anderson | |
| 5,676,673 A | 10/1997 | Ferre | |
| 5,747,996 A * | 5/1998 | Fuchs | 324/207.17 |
| 5,782,765 A | 7/1998 | Jonkman | |
| 5,800,352 A | 9/1998 | Ferre | |
| 5,803,089 A | 9/1998 | Ferre | |
| 5,829,444 A | 11/1998 | Ferre | |
| 5,873,822 A | 2/1999 | Ferre | |
| 5,913,820 A | 6/1999 | Bladen | |
| 5,967,980 A | 10/1999 | Ferre | |
| 6,052,610 A | 4/2000 | Koch | |
| 6,073,043 A | 6/2000 | Schneider | |
| 6,129,668 A | 10/2000 | Haynor | |
| 6,172,499 B1 | 1/2001 | Ashe | |

(Continued)

FOREIGN PATENT DOCUMENTS

WO WO9736192 10/1997

OTHER PUBLICATIONS

Takaaki Nara, et al.; "A Closed-Form Formula for Magnetic Dipole Localization by Measurement of Its Magnetic Field and Spatial Gradients"; Digital Object Identifier; 2006 IEEE; pp. 3291-3293.

*Primary Examiner*—Kenneth J Whittington
(74) *Attorney, Agent, or Firm*—Fletcher Yoder

(57) ABSTRACT

An electromagnetic coil arrangement comprising a plurality of electromagnetic sensors located about the periphery of a region and at least one center electromagnetic sensor located at or near the center of the region, wherein the plurality of electromagnetic sensors and the at least one center electromagnetic sensor are located in a single plane. An electromagnetic tracking system and method of use, the electromagnetic tracking system comprising the electromagnetic coil arrangement, at least one complementary electromagnetic sensor, and a processor configured to process a signal comprising data indicative of a mutual inductance between the at least one complementary electromagnetic sensor and each of the electromagnetic sensors of the electromagnetic coil arrangement.

24 Claims, 7 Drawing Sheets

U.S. PATENT DOCUMENTS

| | | | |
|---|---|---|---|
| 6,175,756 B1 | 1/2001 | Ferre | |
| 6,201,387 B1 | 3/2001 | Govari | |
| 6,226,547 B1 * | 5/2001 | Lockhart et al. | 600/424 |
| 6,246,231 B1 | 6/2001 | Ashe | |
| 6,374,134 B1 | 4/2002 | Bladen | |
| 6,445,943 B1 | 9/2002 | Ferre | |
| 6,502,031 B2 | 12/2002 | Uehara | |
| 6,539,327 B1 | 3/2003 | Dassot | |
| 6,690,963 B2 * | 2/2004 | Ben-Haim et al. | 600/424 |
| 6,701,179 B1 | 3/2004 | Martinelli | |
| 6,774,624 B2 | 8/2004 | Anderson | |
| 6,980,921 B2 | 12/2005 | Anderson | |
| 7,015,859 B2 | 3/2006 | Anderson | |
| 7,096,148 B2 | 8/2006 | Anderson | |
| 7,158,754 B2 | 1/2007 | Anderson | |
| 2004/0046558 A1 * | 3/2004 | Matsumoto | 324/326 |
| 2006/0058604 A1 | 3/2006 | Avinash | |
| 2006/0106292 A1 | 5/2006 | Anderson | |
| 2006/0247511 A1 | 11/2006 | Anderson | |
| 2007/0244388 A1 * | 10/2007 | Sato et al. | 600/424 |
| 2008/0177177 A1 * | 7/2008 | Aoki et al. | 600/424 |

* cited by examiner

COIL ARRANGEMENT FOR ELECTROMAGNETIC TRACKER METHOD AND SYSTEM

BACKGROUND

This disclosure relates generally to tracking systems that use magnetic fields to determine positions and orientations of an object, such as systems used for tracking instruments and devices during surgical interventions and other medical procedures. More particularly, this disclosure relates to a system and method to more accurately determine position and orientation of an object.

Tracking systems have been used in various industries and applications to provide position information relating to objects. For example, electromagnetic tracking may be useful in aviation applications, motion sensing applications, and medical applications. In medical applications, tracking systems have been used to provide an operator (e.g., a physician) with information to assist in the precise and rapid positioning of a medical device located in or near a patient's body. In general, an image may be displayed on a monitor to provide positioning information to an operator. The image may include a visualization of the patient's anatomy with an icon on the image representing the device. As the device is positioned with respect to the patient's body, the displayed image is updated to reflect the correct device coordinates. The base image of the patient's anatomy may be generated either prior to, or during, the medical procedure. For example, any suitable medical imaging technique, such as X-ray, computed tomography (CT), magnetic resonance imaging (MRI), positron emission tomography (PET), and ultrasound, may be utilized to provide the base image displayed during tracking. The combination of the base image and the representation of the tracked device provide positioning information that allows a medical practitioner to manipulate a device to a desired position and/or associate information gathered to a precise location.

To determine device location, tracking systems may utilize a method of electromagnetic (EM) field generation and detection. Using this method, at least one magnetic field is generated from one or more EM sensors, and the magnetic fields are detected by one or more complementary EM sensors. In such a system the mutual inductance of the EM field detected may be processed to resolve a position and/or orientation of the EM sensors relative to one another. For example, an EM sensor may be fixed in a known position, with a complementary EM sensor mounted at the operative end of a device. While the EM sensor generates a magnetic field, the magnetic field characteristics may be detected by the complementary EM sensor. The detected characteristics may be processed to determine the position and orientation (e.g., the X, Y and Z coordinates, as well as the roll, pitch and yaw angles) of the EM sensors relative to one another.

To provide for more accurate device tracking, various arrangements of EM sensors around a tracking area have been used. For example, four EM sensors may be located at the corners of a rectangular region. In this configuration, each of the four EM sensors may generate a magnetic field that is sensed by a complementary EM sensor. A signal indicative of the detected magnetic field characteristic may then be transmitted to a processor. On receipt of the signal, the processor may consider the mutual inductance of each magnetic field sensed to estimate the distance between each EM sensor and each complementary EM sensor. By triangulation, the position and/or orientation of the sensors may be estimated. Other configurations may provide a multitude of EM sensors located about the corners of a cubic volume wherein a complementary EM sensor is tracked in the volume. Although these methods may provide sufficient accuracy, there are several instances in which the sensors located about the periphery do not provide a sufficient estimate of position and/or orientation. For example, where four EM sensors are located at the corners of a rectangular region, the accuracy may vary depending on the location of the complementary sensor being tracked. In this configuration, if the complementary EM sensor is located a significant distance from the plane where four EM sensors are located, the mutual inductance sensed and processed may provide a sufficient position estimate. However, as the complementary EM sensor approaches the plane where the four EM sensors are located, a minimal change in the distance from the plane results in a minimal difference in the mutual inductance sensed between the EM sensors. Accordingly, the small variations in the magnetic field make it difficult for processing to accurately resolve the position of the complementary EM sensors in a direction normal the plane of the four EM sensors.

Accordingly, there is a desire to provide an electromagnetic field tracking system, wherein EM sensors are configured to provide for processing that may accurately determine position and/or orientation of a device.

BRIEF DESCRIPTION

In accordance with one aspect, provided is an electromagnetic coil arrangement, comprising a plurality of electromagnetic sensors located about the periphery of a region and at least one center electromagnetic sensor located at or near the center of the region, wherein the plurality of electromagnetic sensors and the at least one center electromagnetic sensor are located in a single plane.

In accordance with another aspect, provided is an electromagnetic coil arrangement; comprising a plurality of electromagnetic sensors located about the periphery of faces enclosing a volume and at least one center electromagnetic sensor located at or near the center of at least one of the faces.

In accordance with another aspect, provided is an electromagnetic tracking system, comprising an electromagnetic coil arrangement comprising a plurality of electromagnetic sensors located about the periphery of a region and at least one center electromagnetic sensor located at or near the center of the region, wherein the plurality of electromagnetic sensors and the at least one center electromagnetic sensor are located in a single plane, at least one complementary electromagnetic sensor and a processor configured to process a signal comprising data indicative of a mutual inductance between the at least one complementary electromagnetic sensor and each of the electromagnetic sensors of the electromagnetic coil arrangement.

In accordance with yet another aspect, provided is a method of electromagnetic tracking, comprising positioning at least one complementary electromagnetic sensor in a volume of interest with respect to an electromagnetic coil arrangement adjacent to the volume of interest, the coil arrangement comprising a plurality of electromagnetic sensors located about the periphery of a region and at least one center electromagnetic sensor located at or near the center of the region, wherein the plurality of electromagnetic sensors and the at least one center electromagnetic sensor are located in a single plane, sensing a mutual inductance between at least one of the electromagnetic sensors of the electromagnetic coil arrangement and the at least one complementary electromagnetic sensor and processing a signal indicative of the mutual inductance.

DRAWINGS

These and other features, aspects, and advantages will become better understood when the following detailed description is read with reference to the accompanying drawings in which like characters represent like parts throughout the drawings, wherein.

DETAILED DESCRIPTION

Figure 1:
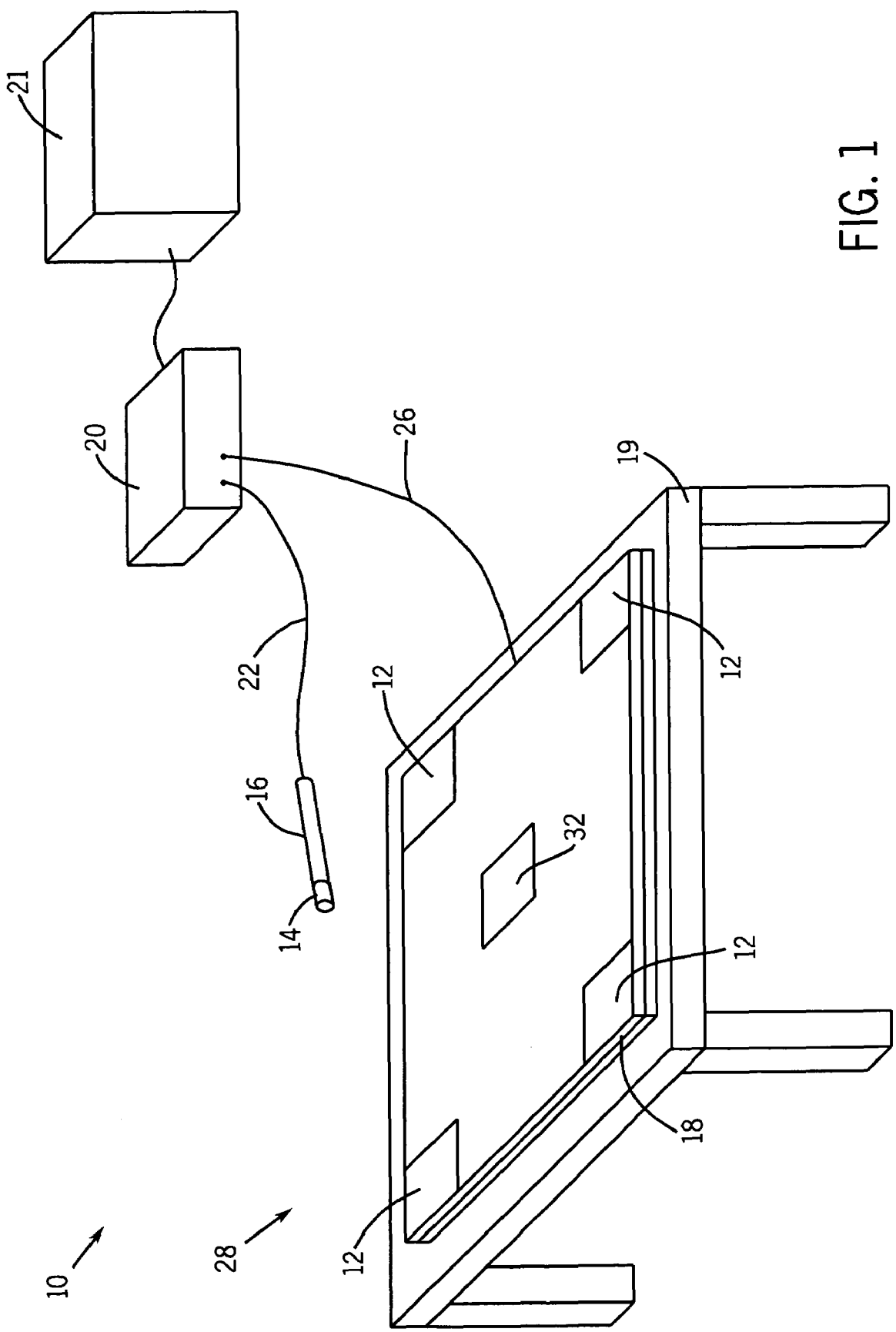
FIG. 1 is an illustration of an exemplary system for magnetic field tracking implementing certain aspects of the present technique.

Referring now to FIG. 1, a tracking system 10 in accordance with one embodiment of the present technique is illustrated. The tracking system 10 may generally include multiple tracking components. As depicted, the tracking components may include an electromagnetic (EM) coil arrangement 28, at least one complementary EM sensor 14, a processor 20 and a user interface 21. The at least one complementary EM sensor 14 may be coupled to at least one instrument 16.

In the illustrated embodiment, the EM coil arrangement 28 comprises a plurality of EM sensors 12 and at least one center EM sensor 32. Generally, the EM sensors 12 and at least one center EM sensor 32 may be formed from magnetic dipoles (e.g., coils, current loops, or electromagnets) capable of producing a dipole magnetic field when a current is applied across them. In some embodiments, the EM sensors (such as the plurality of EM sensors 12 and the at least one center EM sensor 32) may employ industry-standard coil architecture ("ISCA"), a single dipole coil, a planar coil, or a combination of the three. ISCA is defined as three approximately collocated, approximately orthogonal, and approximately dipole coils. EM sensors that are configured with a single coil may generate a single dipole magnetic field, while EM sensors configured with multiple coils may be capable of providing multiple dipole magnetic fields of varying magnitude and direction. By way of example, the EM sensors may be implemented wherein each of the EM sensors includes three orthogonal magnetic dipoles and thus generates a dipole magnetic field in three planes (i.e., X, Y and Z planes).

The magnetic field generated by each of the EM sensors (such as the plurality of EM sensors 12 and the at least one center EM sensor 32) may be dependent upon a current that is provided across the coil of the respective sensor. In one embodiment, to provide a current across the coil, the processor 20 may provide a drive current to each of the EM sensors 12, 32, via cable 26, as illustrated in FIG. 1. As will be appreciated, the EM sensors 12, 32 may also operate in a wireless configuration that does not require a cable connection between the EM sensors 12, 32 and processor 20. With the current flowing across the coil of the EM sensor, the EM sensor may generate at least one dipole magnetic field with a given magnitude and direction. Characteristics of the magnetic field (e.g., magnitude, direction, phase or frequency) may be varied by manipulating the current.

In the depicted system 10, the at least one complementary EM sensor 14 may be configured to sense the magnetic field generated by each of the EM sensors of the EM coil arrangement. For example, sensing the magnetic field may include the at least one complementary EM sensor 14 sensing the mutual inductance of the magnetic field. Embodiments of the at least one complementary EM sensor 14 may include an ISCA, a single dipole coil, a planar coil, or a combination of the three. The coils of the at least one complementary EM sensor 14 coils provide for sensing of the magnetic field data by the at least one complementary EM sensor 14. As will be appreciated, the mutual inductance of EM sensors of the EM coil arrangement 28 (such as the plurality of EM sensors 12 and the at least one center EM sensor 32) and complementary EM sensor 14 are the same, regardless as to which sensors generate the EM field. Therefore, positioning and functionality of the at least one complementary EM sensor 14 with respect to the EM sensor 12 and the at least one center EM sensor 32 in the system 10 may be reversed. For example, in one embodiment, the at least one complementary EM sensor 14 may generate the EM field, while the EM sensors 12 and the at least one center EM sensor 32 are configured to sense the magnetic field. For simplicity, the remainder of this paper may refer to the EM sensors 12 and the at least one center EM sensor 32 as generating a magnetic field, while the at least one complementary EM sensor 14 may be configured to sense the magnetic field.

In either of these configurations, the data gathered by the at least one complementary EM sensor 14 may be processed to determine various parameters. For example, in the illustrated embodiment of FIG. 1, the magnetic field sensed from the at least one complementary EM sensor 14 may be output to a processor 20, via a cable 22. As will be appreciated, the at least one complementary EM sensor 14 may also operate in a wireless configuration that does not require a cable connection between the at least one complementary EM sensor 14 and processor 20. In another embodiment, the processor 20 may monitor the magnetic field sensed by the at least one complementary EM sensor 14 to determine a location (e.g., position and/or orientation) of each complementary EM sensor 14 with respect to the EM coil arrangement 28 and/or the work surface 18.

As mentioned previously, the EM sensors (such as the at least one complementary EM sensor 14, the EM sensors 12, and/or the at least one center EM sensor 32) may be configured as having multiple coils. For example, each of the EM sensors 12 may include three concentric orthogonal dipole coils (coil trios). As will be appreciated, in such an embodiment, a current may be induced across all three coils of the coil trio to simultaneously generate three magnetic fields from an EM sensor 12. The magnetic field generated by each respective coil may be distinguished by varying phase and frequency of each magnetic fields generated. The at least one complementary EM sensor 14 may then sense each of the three magnetic fields generated, and transmit the data received to the processor 20. The processor 20 may distinguish each of the magnetic fields by identifying the respective phase and frequency. As will be appreciated, depending on the number of magnetic fields generated and received, multiple degrees of freedom may be resolved by the processor 20.

For example, wherein an EM sensor 12 and complementary EM sensor 14 each include a coil trio, six degrees of freedom, including three position values and three orientation values may be determined (i.e., X, Y, Z and roll, pitch, yaw).

As illustrated by FIG. 1, the at least one complementary EM sensor 14 may be coupled to the at least one instrument 16. In medical tracking applications, the at least one instrument 16 may include devices used during a medical procedure. As will be appreciated by a person of ordinary skill in the art, the present technique may be used to track a variety of instruments 16 and devices used during medical procedures. For example, the at least one instrument 16 may be a drill, a guide wire, a catheter, an endoscope, a laparoscope, a biopsy needle, an ablation device or other medical devices.

In general, the processor 20 may perform several functions in the tracking system 10. For example, the processor 20 may include electronic circuitry to provide the drive signals, electronic circuitry to receive the sensed signals, and electronic circuitry to condition the drive signals and the sensed signals. Further, the processor 20 may include processing to coordinate functions of the system 10, to implement navigation and visualization algorithms suitable for tracking and displaying the position and orientation of an instrument or device on a monitor. The processor may include a digital signal processor, memory, a central processing unit (CPU) or the like, for processing the acquired signals. As will be appreciated, the processing may include the use of one or more computers within the processor 20. The addition of a separate CPU may provide additional functions for tracking, including, but not limited to, signal processing of data received, and transmission of data to the user interface 21, including a display. In one embodiment, the CPU may be confined within the processor 20, while in another embodiment a CPU may include a stand-alone device that is separate from the processor 20.

As mentioned, system 10 may also include a user interface 21. For example, the system 10 may include a monitor configured to display the position and orientation of at least one instrument 16 or device. Thus, a medical practitioner may monitor the position of the at least one tracked instrument 16 or device on the user interface 21. As will be appreciated, the user interface 21 may also include additional devices to facilitate the exchange of data between the system 10 and the user. For example, the user interface may include a keyboard, mouse, printers or other peripherals. While the processor 20 and the user interface 21 may be separate devices, in certain embodiments, the processor 20 and the user interface may be provided as a single unit.

Returning now to the processing of the data received, the processor 20 may use an iterative approach to arrive at a determined position and orientation of the at least one instrument 16. For example, an initial "seed" approximation of position and orientation may be provided, or resolved by initial measurements of the system 10 and the processor 20. The processor 20 may then use this approximate position and orientation in subsequent algorithms to predict the electric field characteristics and to determine a new estimate of position. The processor 20 may then consider calculating new estimates of the magnetic field characteristics. The iteration of estimating and comparing may continue until the estimated values are sufficiently similar to the position and orientation actually sensed.

Accordingly, it is desirable that the system 10 be configured to ensure that a determination of position and orientation be done efficiently and accurately. For example, to increase the accuracy of the seed approximation, as well as the measured values of the electromagnetic fields, the number of EM sensors 12 may be increased. By increasing the number of EM sensors 12, the volume may more accurately be represented. This is true under fundamental equations and magnetism, because the magnetic field magnitude varies inversely with the cube of distance to the source of the magnetic field. As will be appreciated, the greater variation of magnetic field characteristics essentially increases the resolution for determining position. Therefore, as the number of EM sensors 12 increases around a given tracking area or volume, the detected changes, and thereby location, should be more pronounced to increase accuracy.

In various electromagnetic tracking systems, numerous configurations of EM sensors 12 may be employed. As discussed briefly above, one instance may include a plurality of EM sensors 12 located about the periphery of a region. For example, four EM sensors 12 may be located at the corners of table 19 for tracking the position of at least one complementary EM sensor 14 that is attached to at least one instrument 16 or device. In this scheme of tracking, the various magnetic fields generated by the EM sensors 12, may be sensed by the at least one complementary EM sensor 14 and the data returned to processor 20 for processing. In many instances, this configuration may provide sufficient accuracy to determine position of the at least one complementary EM sensor 14 and the at least one instrument 16. For example, when the at least one complementary EM sensor 14 is located at a reasonable distance from the plane containing the EM sensors 12, the sensed inductance may be used to estimate the distance of the at least one complementary EM sensor 14 from each of the EM sensors 12 and, then, calculate a position of the at least one complementary EM sensor 14 using triangulation. However, as the at least one complementary EM sensor 14 approaches the plane where the EM sensors 12 are located, a given change in the distance from the plane results in a minimal difference in the mutual inductance sensed between the EM sensors 12 and the at least one complementary EM sensors 14. This shortcoming is more pronounced as the at least one complementary EM sensor 14 nears a location at the center of the plane where the mutual inductance from each of the EM sensors 12 may vary at a smaller amount. Accordingly, the small variations in the magnetic field make it difficult for processing to accurately resolve the position of the at least one complementary EM sensor 14 in a direction normal the plane where the four EM sensors 12 are located. For example, traditional calculations may lead to results containing imaginary numbers that are incapable of reflecting the actual position of the at least one complementary EM sensor 14. Accordingly, there is a desire to provide an electromagnetic field tracking system wherein multiple EM sensors are configured to provide for processing that may accurately determine position and/or orientation of a device.

Figure 2:
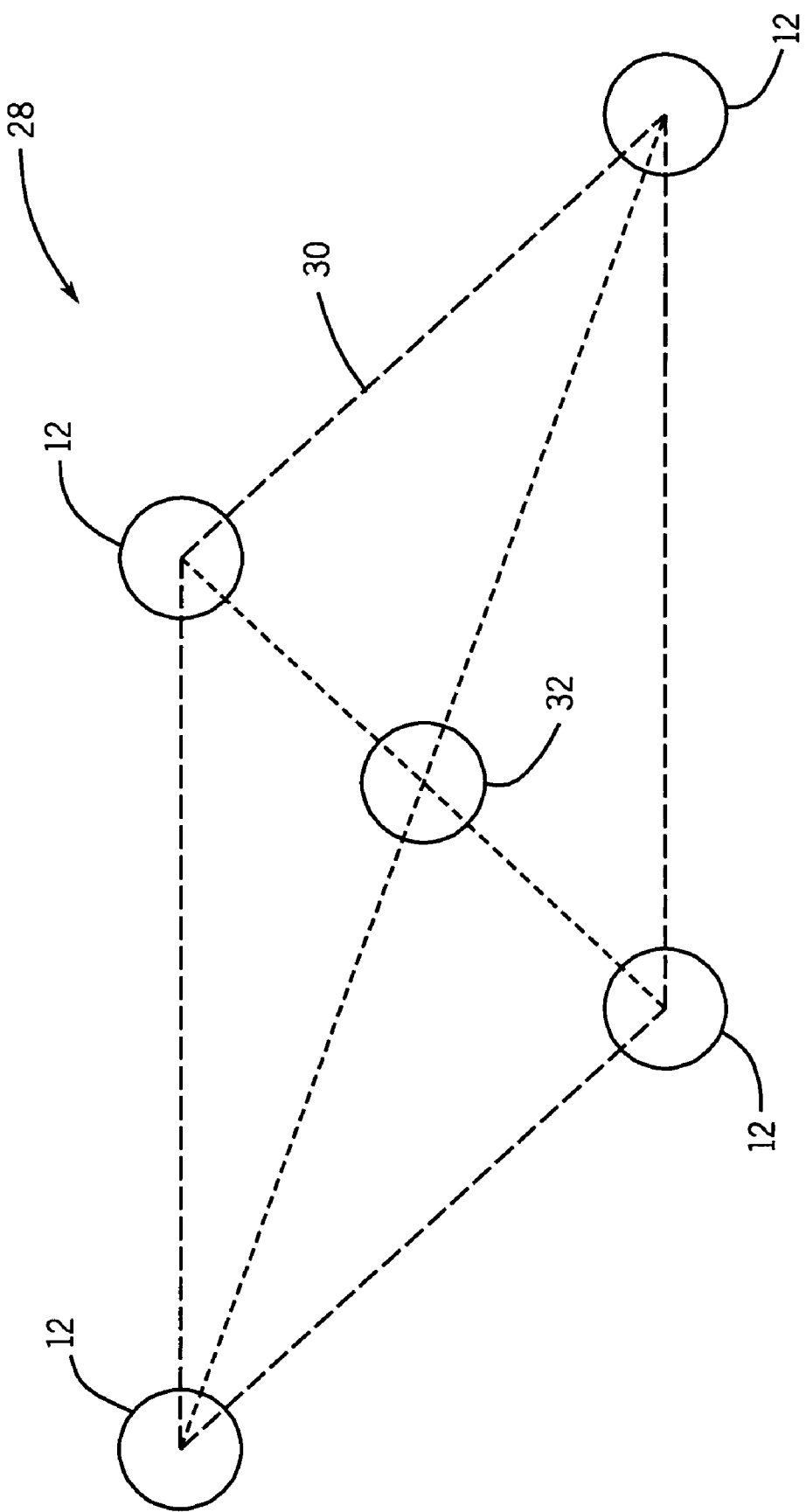
FIG. 2 is an illustration of an exemplary coil arrangement in accordance with certain aspects of the present technique.

Turning now to FIG. 2, an EM coil arrangement 28 in accordance with an exemplary embodiment of the present technique is depicted. In an embodiment, a plurality of EM sensors 12 may be arranged about the periphery of a region 30, with at least one center EM sensor 32 located in center of the region 30. The embodiment may include EM sensors 12 and the at least one center EM sensor 32 all being located in the same plane (e.g., on top of a surgery table or on the surface of a printed circuit board). For example, as depicted in FIG. 2, four EM sensors 12 may be located at the corners of a rectangular region 30, with an at least one center EM sensor 32 located at the center of the region 30. While the at least one center EM sensor 32 is illustrated at the center of the region 30, those of ordinary skill in the art will appreciate that positioning the at least one center EM sensor 32 near the center, will also increase tracking accuracy.

In the embodiment illustrated by FIG. 2, the at least one center EM sensor 32 may provide for generation and sensing of an additional magnetic field. The sensed inductance of this magnetic field may be included in processing to provide an additional constraint to provide for more accurately determining the position and/or location of the at least one complementary EM sensor 14. As will be appreciated by a person of ordinary skill in the art, the region 30 may vary in shape to accommodate various tracking areas. For example, the region 30 may be defined by a circular area, a polygon, or even a free form shape defined by the region it encompasses. As will also be appreciated by a person of ordinary skill in the art, the number of EM sensors 12 may be varied to accommodate various applications. For example, eight EM sensors 12 (not shown) may be positioned about the perimeter of a rectangular region, such as region 30 depicted in FIG. 2. Further, in accordance with prior discussions, a person or ordinary skill in the art will appreciate that the EM sensors 12 and the at least one center EM sensor 32 may each include single dipole coils, planar coils, a coil trio, or any combination thereof.

Figure 3:
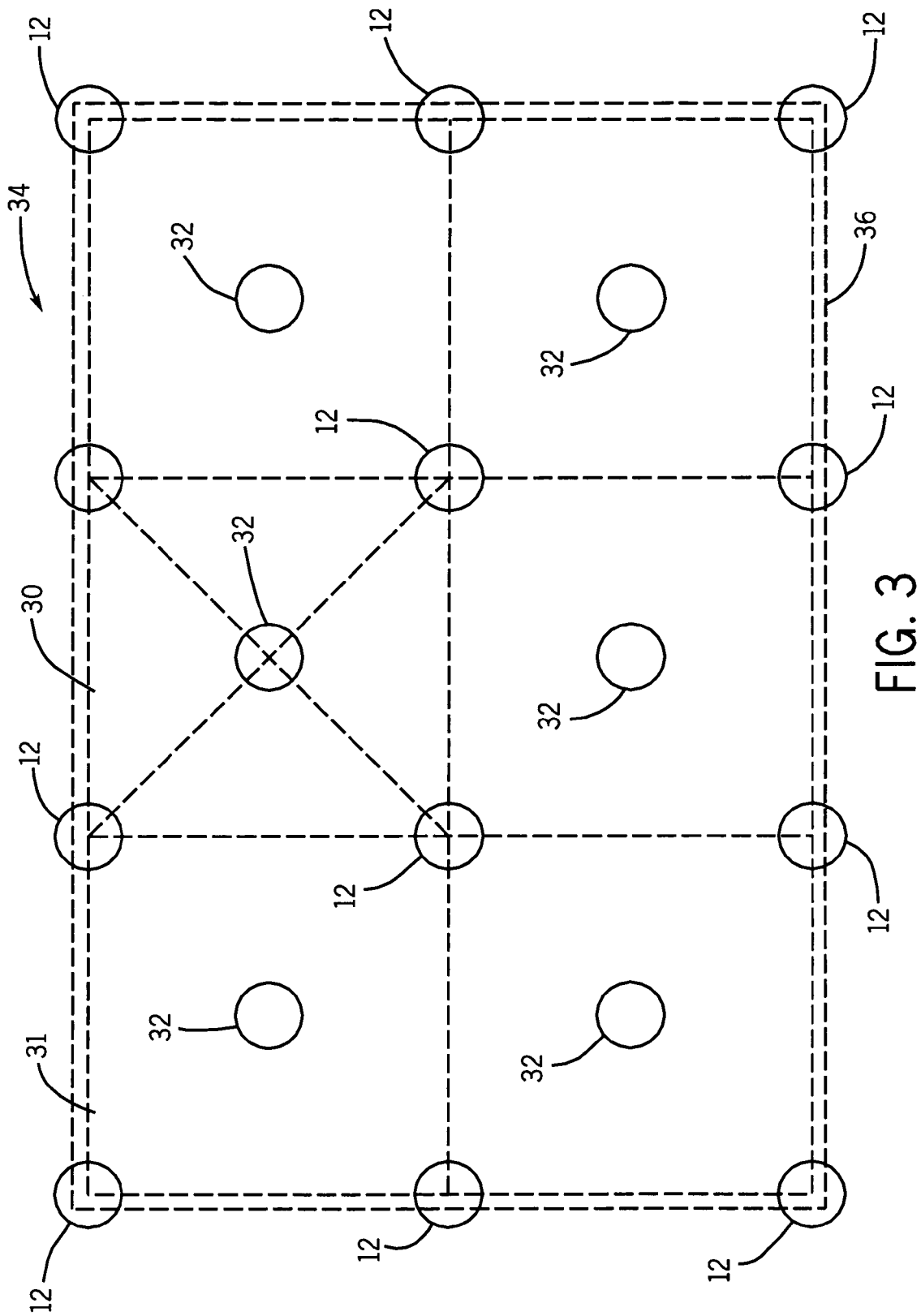
FIG. 3 is an illustration of an exemplary coil arrangement, wherein a plurality of sensors form a grid in accordance with certain aspects of the present technique.

To increase the area of the tracking volume accurately covered by the tracking arrangement depicted in FIG. 2, a plurality of EM coil arrangements 28, as shown in FIG. 2, may be provided as an arranged array 34, as depicted in FIG. 3. In one embodiment, the arranged array 34 may include a plurality of EM coil arrangements 28 located in a single plane. For example, as depicted in FIG. 3, six arrangements 28 may be located in a single array region 36.

Figure 4:
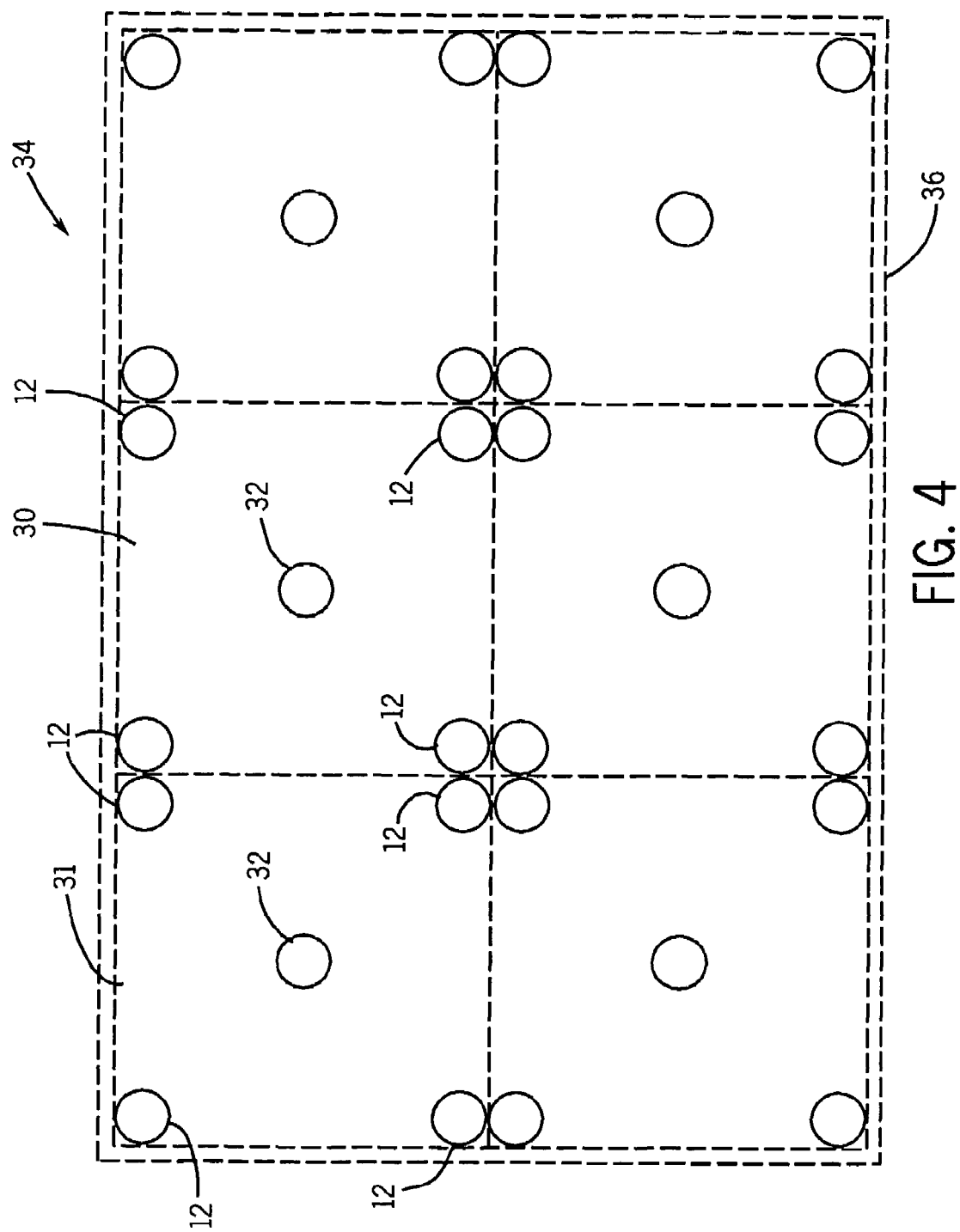
FIG. 4 is an illustration of an alternate coil arrangement, wherein a plurality of sensors form a grid in accordance with certain aspects of the present technique.

Further, an embodiment of an arranged array 34 may include two adjacent regions 30 sharing two EM sensors 12 about their periphery. For example, as depicted in FIG. 3, a first region 30 may be adjacent to a second region 31. In this embodiment, the first region 30 and the second region 31 may share two EM sensors 12 that are used in conjunction with the center EM sensors 32 of the first region 30 and the second region 31. As will be appreciated by a person of ordinary skill in the art, the configuration of the arranged array 34 may by varied to accommodate specific applications. For example, it may be desirable for each of the arrangements 28 in the array region to not share EM sensors 12. In an embodiment depicted by FIG. 4, although the regions 30 abut one another, each region may include its own set of four EM sensors 12 and center EM sensor 32. This may be advantageous for a tracking system 10 with arrangements 28 that are modular. For example, the arrangements 28 may include separable units that may be stacked side-by-side, or removed from to create an array region 36 of increased or decreased area. As will be appreciated by a person of ordinary skill in the art, the number of arrangements 28 in the arranged array 34, the shape of the regions 30 and 31, the shape and size of the arranged array region 36, and the configuration of the EM sensors 12 may be varied and/or combined to accommodate various applications.

Figure 5:
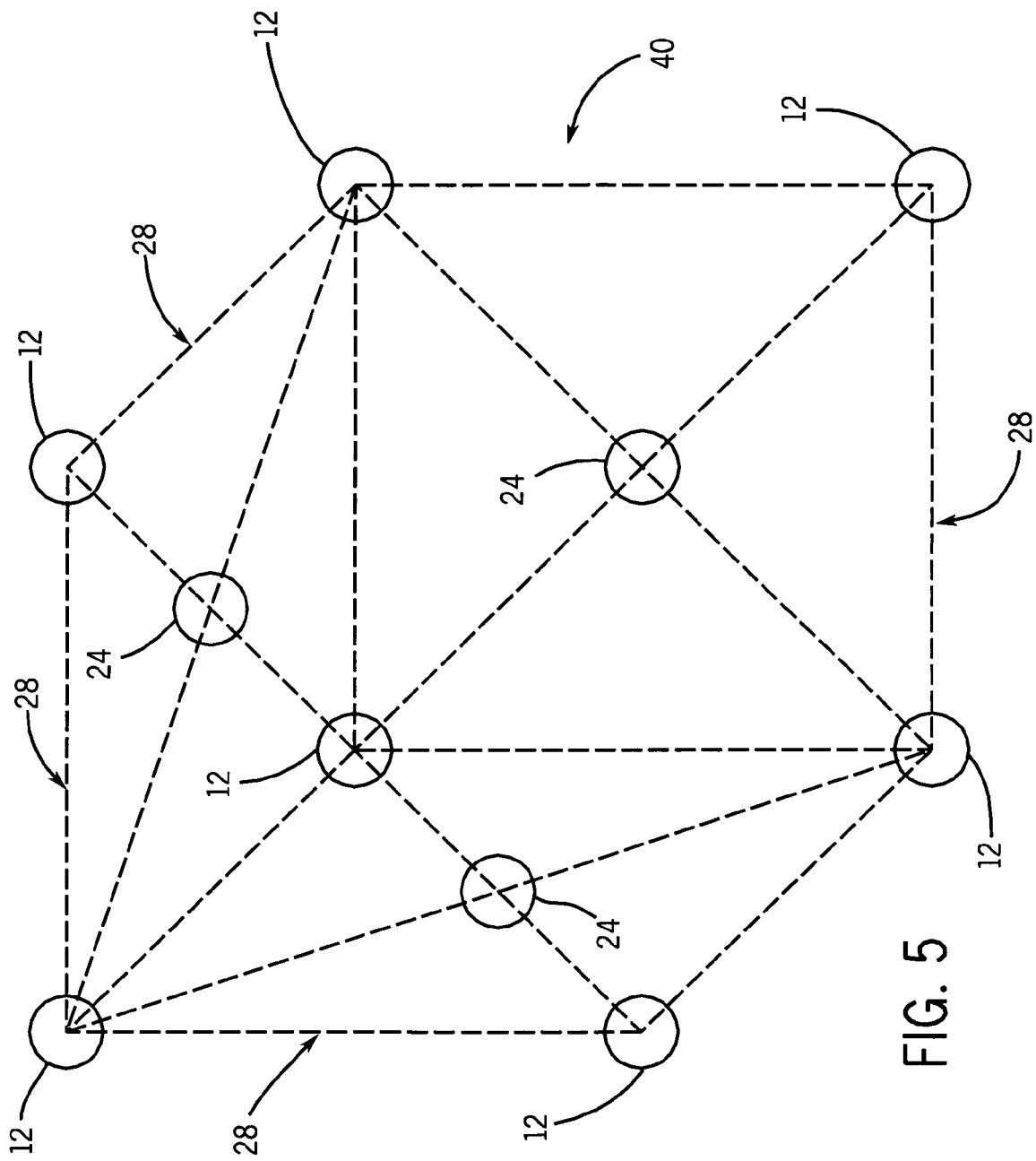
FIG. 5 is an illustration of an exemplary coil arrangement, wherein a plurality of sensors enclose a volume in accordance with certain aspects of the present technique.

Turning now to FIG. 5, depicted is a volume enclosed by multiple EM coil arrangements 28. In an embodiment, it may be desirable to enclose a volume with EM sensors 12 to provide tracking in or near an enclosed volume 40. For example, as depicted by FIG. 5, the volume 40 may comprise faces forming a substantially hexahedron configuration. In such an embodiment, EM coil arrangements 28 may be positioned about the faces of the volume 40 such that the EM sensors 12 are located about the periphery of the faces of the volume 40 and at least one center EM sensor 32 is located at or near the center of at least one of the faces. This configuration may prove advantageous in similar situations as to those described previously. For example, as a complementary EM sensor 14 approaches the center region of a face of the volume 40, the system 10 may have difficulty processing the minute differences in mutual inductances used to estimate differences. As a result, the processor 20 may not accurately resolve a position of the at least one complementary EM sensor 14. The addition of at least one center EM sensor 32 on a face may increase the accuracy. As will be appreciated, not all of the faces or locations on a volume may include the at least one center EM sensor 32. For example, in one embodiment, it may be desirable to pass and object (i.e., a patient on a surgery room table) through one, or a multitude, of faces of the volume 40. In such an embodiment, it may be necessary to include an arrangement 28 with at least one center EM sensor 32 only on the faces of the volume where tracking near the face of the volume 40 may be desired, and no obstruction is present. Further, as will be appreciated by a person or ordinary skill in the art, in other embodiments, the shape of the volume may take various forms. For example, the volume may include a substantially spherical shape that is enclosed by a multitude of EM coil arrangements 28, or other polyhedrons that may be enclosed by multiple EM coil arrangements 28.

Figure 6:
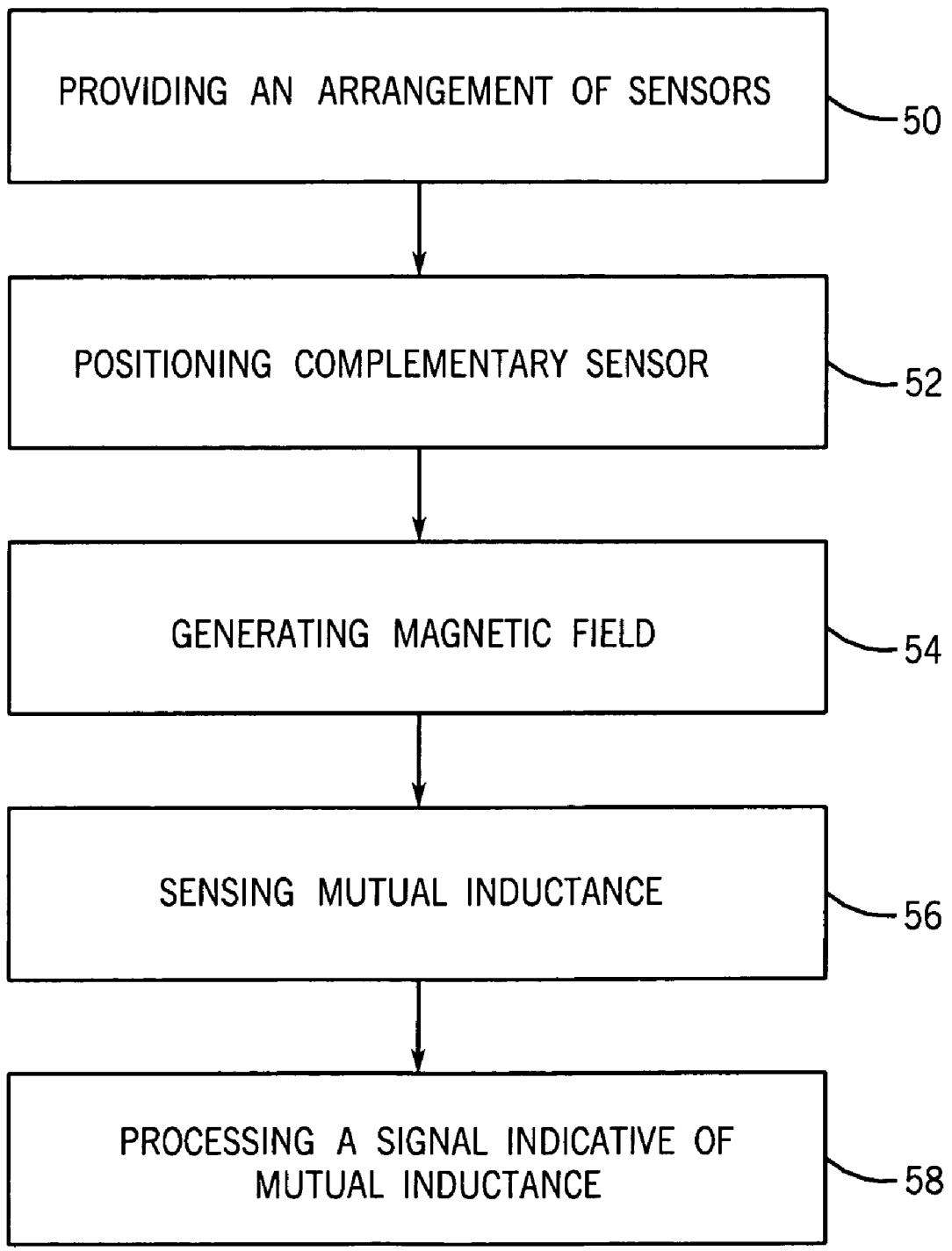
FIG. 6 is a flowchart depicting a method of electromagnetic tracking in accordance with certain aspects of the present technique.

A method of using the EM tracking system 10 is depicted in flowchart form in FIG. 6. As described above, an electromagnetic tracking system 10 may include an EM coil arrangement 28 and a complementary EM sensor 14. As previously mentioned, the EM coil arrangement 28 comprises a plurality of EM sensors 12 located about the periphery of a region 30 and at least one center EM sensor 32 located at or near the center of region 30. In such an embodiment, either of the EM sensors 12, the at least one center EM sensor 32 or the at least one complementary EM sensor 14 may generate a magnetic field which is sensed by the other EM sensors. The sensed signal may be provided to a processor 20 to determine a parameter, such as position and/or orientation of the sensors 12, 14, 32 relative to one another. Accordingly, FIG. 6 depicts the step of providing the EM coil arrangement 28 located adjacent to a volume of interest as depicted at block 50. As will be appreciated by a person of ordinary skill in the art, the EM coil arrangement 28 may be provided in various configurations, including those described previously. For example, the region 30, as well as the number of EM sensors 12, 14, 32 may be varied to meet the requirements of the system 10, such as fully covering the anticipated area of tracking. Additionally, the type of coils used to form the EM sensors 12, 14, 32 may include a single dipole coil, a planar coil, a coil trio, or any combination thereof.

As depicted at block 52, FIG. 6 further illustrates an embodiment which includes positioning a complementary sensor 14 in the volume of internet with respect to the EM coil arrangement. As described previously, the at least one complementary EM sensor 14 may be coupled to at least one instrument 16 tracked by the system 10. Further, different types of coils may be used to form the at least one complementary EM sensor 14. Coil types may include a single dipole coil, a planar coil, a coil trio, or any combination thereof. As mentioned previously, the mutual inductance of EM sensors 12 and complementary EM sensor 14 are the same, regardless as to which senor is the complementary EM sensor 14 and which sensor is the EM sensor 12. Accordingly, it will be appreciated by a person of ordinary skill in the art that the steps of providing an arrangement of sensors and providing complementary sensor, may be accomplished in any order, or configuration of sensors.

Returning to FIG. 6, an embodiment of the method further includes generating magnetic field, as depicted at block 54. Embodiments of the method include generating a single magnetic field, or generating a multitude of magnetic fields. For example, as discussed previously, the number of magnetic fields generated and detected may be increased in number to resolve an increased number of degrees of freedom, or may be increased to improve the accuracy of the system 10. Further, the method of generating a magnetic field may be provided by generation from the EM sensors 12, 32 or the at least one complementary EM sensor 14.

In another embodiment, the method may also include sensing the mutual inductance of the generated magnetic field, as depicted at block 56. As will be appreciated by a person of ordinary skill in the art, the mutual inductance between EM sensors 12, the at least one center EM sensor 32 and/or the at least one complementary EM sensor 14, is the same no matter which one generates the magnetic field. Therefore, the discussions relating to the variation on generating magnetic fields also are consistent with sensing mutual inductance of the magnetic field (i.e., varying the number and type of EM sensors 12, 14, 32). Sensing mutual inductance of the magnetic field may also comprise providing a signal that is indicative of the detected mutual inductance, to a processor 20 for processing. For example, a complementary EM sensor 14 may sense the mutual inductance of the magnetic field(s) generated by the EM sensors 12, and may convert the sensed characteristics to an electrical signal that is indicative of the sensed characteristics. In one embodiment, the electrical signal may include a modulated signal that is demodulated and processed by the processor 20.

As will be appreciated, processing the signal indicative of the mutual inductance may be performed to resolve a desired parameter. For example, the embodiment of the method in FIG. 6 includes processing a signal indicative of the mutual inductance to determine a position and/or orientation of the sensors, as depicted at block 58. Processing may include the processor 20 receiving data, including a signal indicative of the mutual inductance sensed, and performing several functions to arrive at a resolved position and/or orientation. In an electromagnetic tracking system 10, processing may take several different forms. For example, in one embodiment, the mutual inductance between each EM sensor 12 and complementary EM sensor 14 may be equated to a distance. The distances may then be used to generate a "seed guess" of approximate position. This seed guess may then be used in processing of algorithms to determine a calculated electromagnetic field which is based on the known positions of the EM sensors 12 and the complementary EM sensor 14 fixed about the tracking area. In one embodiment, processing may include the completion of several iterations of the measuring and comparing process until the sensed values are within a given range of error as compared to the calculated values. When the values approximately "match," the processor 20 may output the data as the resolved position and/or orientation. In another embodiment, processing to determine a position and/or orientation of the sensors may include processing the data for output to a user interface 21. For example, processing may include outputting the position data in the form of an image to a monitor. The image output may comprise the position resolved, represented by an icon overlaid on an image representing a patient.

Figure 7:
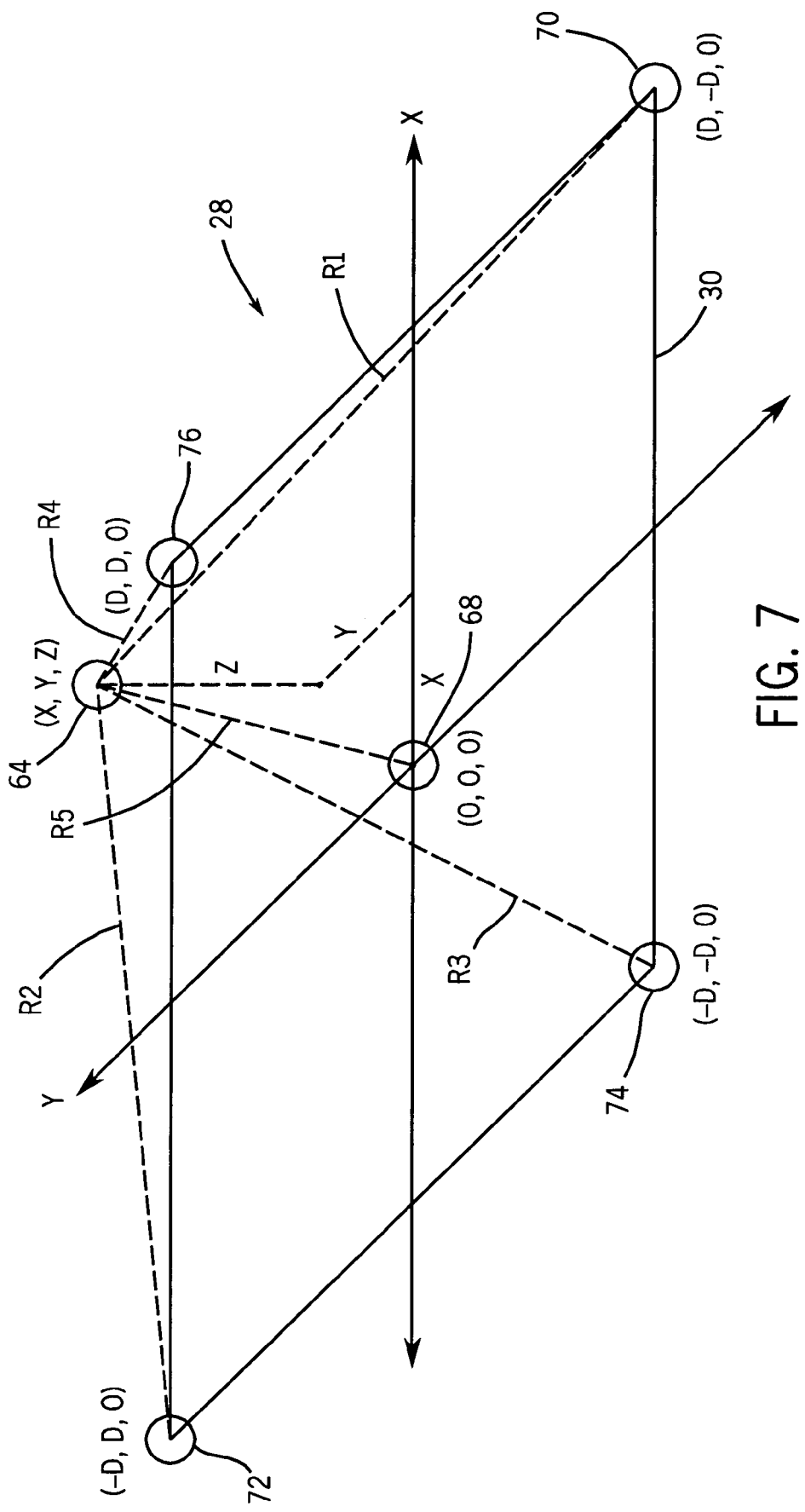
FIG. 7 is an illustration of the considerations for determining position of a sensor in accordance with certain aspects of the present technique.

As mentioned previously, the EM coil arrangement 28 comprising EM sensors 12 about the periphery of a region 30 and a center EM sensor 32, may be most beneficial to the ability of processing to accurately resolve a position and/or orientation. For example, this may best be demonstrated by a method used to equate the sensed mutual inductances to distances, and combine the distances in multiple dimensions to triangulate a position and/or orientation. As previously stated, processing 58 may include, first, determining the position of a complementary EM sensor 14 to provide a seed guess for subsequent calculations. For example, as depicted in FIG. 6, one embodiment may include complementary EM sensor 64, formed from a single dipole coil with a known effective area ($A_{effe}$). The complementary EM sensor 64 may be positioned above a single plane containing an arrangement 28 of five EM sensors 68, 70, 72, 74, 76, wherein each of the five EM sensors 68, 70, 72, 74, 76 are formed from a coil trio with an known effective area ($A_{effe}$). The arrangement of five EM sensors 68, 70, 72, 74, 76 may include four EM sensors 70, 72, 74, 76 located at the corners of a square region 30, with a center EM sensor 68 located near the center of the square region 30. The positions in a three dimensional coordinate system may be defined as first EM sensor 70 located at (D,−D,0), second EM sensor 72 located at (−D,D,0), third EM sensor 74 located at (−D,−D,0), fourth EM sensor 76 located at (D, D, 0), and the center EM sensor 68 located at (0,0,0). The position of the complementary EM sensor 64 may be defined as (x,y,z) above the square region. In this configuration, the distance from the complementary EM sensor 64 to each EM sensor of the arrangement 28 may be defined as follows (see FIG. 7):

$R_1$=distance from first EM sensor 70 to complementary EM sensor 64

$R_2$=distance from second EM sensor 72 to complementary EM sensor 64

$R_3$=distance from third EM sensor 74 to complementary EM sensor 64

$R_4$=distance from forth EM sensor 76 to complementary EM sensor 64

$R_5$=distance from center EM sensor 68 to complementary EM sensor 64

The mutual inductance between the complementary EM sensor 64 and one of the EM sensors 68, 70, 72, 74, 76 of the arrangement 28 may be given by:

$$L = \frac{\mu_o \times A_{effc} \times A_{effe}}{R^3} \times C_1 \qquad (80)$$

Wherein:
L=mutual inductance magnitude in henries
$\mu_o$=the permeability of free space=$\Pi*4\times10^{-7}$ henries/meter
R=distance between sensors
$C_1$=a factor from 1 to 2 that may be determined based upon the orientation of the generating sensor.

Wherein $C_1$ is equal to the square root of two, equation 80 may be approximated:

$$L = \frac{\mu_o \times A_{effc} \times A_{effe}}{R^3} \times \sqrt{2} \qquad (82)$$

Solving equation 82 for the distance R gives:

$$R = \sqrt[3]{\frac{\mu_o \times A_{effc} \times A_{effe} \times \sqrt{2}}{L}} \qquad (84)$$

Using equation 84 and the mutual-inductance sensed from each respective sensor, the approximate distances, $R_1$, $R_2$, $R_3$, $R_4$, and $R_5$ may be calculated. By triangulation of the distances, it may determined:

$$x = \frac{R_2^2 - R_4^2 + R_3^2 - R_1^2}{8D} \quad (86)$$

$$y = \frac{R_1^2 - R_4^2 + R_3^2 - R_2^2}{8D} \quad (88)$$

At this point in the processing, the benefit of the center EM sensor 32 may become evident. For example, if only four sensors are used at the corners of the rectangular region 30 and $R_5$ is not known, a square root is needed to calculate the z component of the complementary EM sensor 64 location:

$$z = \sqrt{\frac{R_4^2 + R_1^2 + R_3^2 + R_2^2 - 4x^2 - 4y^2}{4}} \quad (90)$$

As the actual position of the complementary EM sensor 64 approaches the plane that includes the four EM sensors 70, 72, 74, 76, equation 90 may produce inaccurate z position determinations. In addition, the inaccuracy may include incomprehensible imaginary results if the numerator of equation 90 is negative and therefore results in the square root of a negative number.

To improve the accuracy of the position determination in the z axis, the addition of the center EM sensor 68 may provide for more accurate and reliable results. For example, the addition of a center EM sensor 68 may provide for the following direct calculation of distance based on the center EM sensor 76:

$$z = \sqrt{\frac{R_5^2 - x^2 - y^2}{4}} \quad (92)$$

Under equation 92, if solving for z results in an imaginary number the value for z may be set to zero.

As described previously, the processor 20 may implement the above technique to determine an approximate position for the complementary EM sensor 64 which is being tracked by the system 10. This initial position estimate (i.e., "seed guess") may be used as the determined position or in subsequent algorithms to more accurately determine the position and/or orientation of the complementary EM sensor 64.

While only certain features of the technique have been illustrated and described herein, many modifications and changes will occur to those skilled in the art. It is, therefore, to be understood that the appended claims are intended to cover all such modifications and changes as fall within the true spirit of the invention.

The invention claimed is:

1. An electromagnetic coil arrangement, comprising:
a plurality of modular units, wherein each modular unit of the plurality of modular units includes:
   a plurality of electromagnetic sensors located about the periphery of a region; and
   at least one center electromagnetic sensor located at or near the center of the region;
   wherein the plurality of electromagnetic sensors and the at least one center electromagnetic sensor are located in a single plane; and
   wherein each modular unit is configured to be selectively removed from or added to other modular units of the plurality of modular units to form an electromagnetic tracking array located in a single plane adjacent a volume of interest and to facilitate variation of at least one of the size or the shape of the electromagnetic tracking array.

2. The electromagnetic coil arrangement of claim 1, wherein each of the electromagnetic sensors comprises a single dipole electromagnetic coil or an electromagnetic coil trio.

3. The electromagnetic coil arrangement of claim 1, wherein each of the electromagnetic sensors is configured to generate at least one magnetic field.

4. The electromagnetic coil arrangement of claim 1, wherein each of the electromagnetic sensors is configured to sense at least one magnetic field.

5. The electromagnetic coil arrangement of claim 1, wherein at least two modular units of the plurality of modular units are positioned adjacent one another such that the respective at least one center electromagnetic sensors and the respective pluralities of electromagnetic sensors of the at least two modular units are coplanar.

6. The electromagnetic coil arrangement of claim 5, wherein the at least two modular units positioned adjacent one another do not share a common electromagnetic sensor.

7. An electromagnetic tracking system, comprising:
an electromagnetic coil arrangement comprising a plurality of modular units each including: a plurality of electromagnetic sensors located about the periphery of a region and at least one center electromagnetic sensor located at or near the center of the region, wherein the plurality of electromagnetic sensors and the at least one center electromagnetic sensor are located in a single plane and wherein each modular unit is configured to be selectively removed from or added to other modular units to form an electromagnetic tracking array located in a single plane adjacent a volume of interest and to facilitate variation of at least one of the size or the shape of the electromagnetic tracking array;
at least one complementary electromagnetic sensor; and
a processor configured to process a signal comprising data indicative of a mutual inductance between the at least one complementary electromagnetic sensor and each of the electromagnetic sensors located within the single plane of the electromagnetic tracking array.

8. The electromagnetic tracking system of claim 7, wherein each of the electromagnetic sensors comprises a single dipole electromagnetic coil or an electromagnetic coil trio.

9. The electromagnetic tracking system of claim 7, wherein the at least one complementary electromagnetic sensor comprises a single dipole electromagnetic coil or an electromagnetic coil trio.

10. The electromagnetic tracking system of claim 7, wherein each of the electromagnetic sensors of the electromagnetic coil arrangement is configured to generate at least one magnetic field, and wherein the at least one complementary electromagnetic sensor is configured to sense at least one magnetic field.

11. The electromagnetic tracking system of claim 7, wherein each of the electromagnetic sensors of the electromagnetic coil arrangement is configured to sense at least one magnetic field, and wherein the at least one complementary electromagnetic sensor is configured to generate at least one magnetic field.

12. The electromagnetic tracking system of claim 7, wherein the processor is configured to determine position and/or orientation of the at least one complementary electromagnetic sensor.

13. The electromagnetic tracking system of claim 12, wherein the processor is configured to use triangulation to determine position and/or orientation, wherein triangulation comprises using ratios of mutual inductance sensed between each of the electromagnetic sensors of the electromagnetic coil arrangement and the at least one complementary electromagnetic sensor to determine position and/or orientation of the at least one complementary electromagnetic sensor.

14. The electromagnetic tracking system of claim 12, wherein the processor is configured to use the position and/or orientation as an estimate of position for use in subsequent processing.

15. The electromagnetic tracking system of claim 12, comprising a display configured to display the position and/or orientation of a medical instrument or a medical device.

16. The electromagnetic tracking system of claim 7, wherein the at least one complementary electromagnetic sensor is coupled to a medical device.

17. A method of electromagnetic tracking, comprising:
positioning at least one complementary electromagnetic sensor in a volume of interest with respect to an electromagnetic coil arrangement adjacent to the volume of interest, the coil arrangement comprising a tracking array of coplanar modular units each including: a plurality of electromagnetic sensors located about the periphery of a region and at least one center electromagnetic sensor located at or near the center of the region, wherein the plurality of electromagnetic sensors and the at least one center electromagnetic sensor are located in a single common plane of the tracking array and wherein each modular unit is configured to be separable from other modular units of the tracking array of coplanar modular units to facilitate variation of at least one of the size or the shape of the electromagnetic coil arrangement within the common plane;
sensing a mutual inductance between at least one of the electromagnetic sensors of the electromagnetic coil arrangement and the at least one complementary electromagnetic sensor; and
processing a signal indicative of the mutual inductance.

18. The method of electromagnetic tracking of claim 17, wherein the at least one complementary electromagnetic sensor is coupled to a medical device.

19. The method of electromagnetic tracking of claim 17, wherein each of the electromagnetic sensors of the electromagnetic coil arrangement generate at least one magnetic field, and wherein sensing a mutual inductance comprises the at least one complementary electromagnetic sensor sensing at least one magnetic field.

20. The method of electromagnetic tracking of claim 17, wherein the at least one complementary electromagnetic sensor generates at least one magnetic field, and wherein sensing a mutual inductance comprises at least one of the electromagnetic sensors of the electromagnetic coil arrangement sensing a magnetic field.

21. The method of electromagnetic tracking of claim 17, wherein processing a signal indicative of mutual inductance of the magnetic field comprises determining a position and/or orientation of the at least one complementary electromagnetic sensor.

22. The method of electromagnetic tracking of claim 21, wherein determining the position and/or orientation comprises triangulation via ratios of mutual inductance sensed between the electromagnetic sensors of the electromagnetic coil arrangement and the at least one complementary electromagnetic sensor.

23. The method of electromagnetic tracking of claim 17, comprising displaying the position and/or orientation on a monitor.

24. The method of electromagnetic tracking of claim 17, wherein processing a signal indicative of the mutual inductance comprises solving for the distance between sensors, R, in the equation:

$$L = \frac{\mu_o \times A_{effc} \times A_{effe}}{R^3} \times C_1$$

and wherein:
L=mutual inductance magnitude in henries
$\mu_O$=the permeability of free space =$\Pi*4\times10^{-7}$ henries/meter
R =distance between sensors
$C_1$=a factor between 1 and 2 that may be determined based upon the orientation of the generating sensor.

* * * * *